(12) United States Patent
Souter et al.

(10) Patent No.: US 7,153,438 B2
(45) Date of Patent: Dec. 26, 2006

(54) WATER TREATMENT COMPOSITIONS WITH MASKING AGENT

(75) Inventors: Philip Frank Souter, Morpeth (GB); Colin Ure, Wallsend (GB)

(73) Assignee: Pur Water Purification Products, Inc., Cincinnati, OH (US)

( * ) Notice: Subject to any disclaimer, the term of this patent is extended or adjusted under 35 U.S.C. 154(b) by 0 days.

(21) Appl. No.: 10/371,864

(22) Filed: Feb. 21, 2003

(65) Prior Publication Data

US 2004/0164029 A1 Aug. 26, 2004

(51) Int. Cl.
  *C02F 1/76* (2006.01)
  *C02F 1/56* (2006.01)
  *C01B 11/06* (2006.01)

(52) U.S. Cl. .............. 210/764; 210/756; 252/187.27; 252/187.28; 252/187.24; 252/187.29; 252/187.3; 252/187.33; 252/187.34; 512/4; 512/3; 512/2; 510/302; 510/367; 510/377; 510/382

(58) Field of Classification Search ............. 252/187.1, 252/187.2, 187.23, 187.24, 187.25, 187.26, 252/187.27, 187.28, 187.29, 187.3, 187.31, 252/187.32, 187.33, 187.34, 179; 510/302, 510/367, 377, 382; 210/764, 756; 512/4, 512/3, 2

See application file for complete search history.

(56) References Cited

U.S. PATENT DOCUMENTS

| | | | | |
|---|---|---|---|---|
| 3,108,079 A * | 10/1963 | Wixon | ......................... | 510/302 |
| 4,735,803 A * | 4/1988 | Katz et al. | ................... | 424/409 |
| 5,075,025 A * | 12/1991 | Wainberg et al. | ........... | 424/665 |
| 5,238,344 A * | 8/1993 | Nagayama | .................. | 411/183 |
| 5,691,303 A * | 11/1997 | Pan et al. | ....................... | 512/4 |
| 5,858,959 A * | 1/1999 | Surutzidis et al. | .......... | 510/507 |
| 5,955,419 A * | 9/1999 | Barket et al. | ................ | 510/507 |
| 6,025,319 A * | 2/2000 | Surutzidis et al. | .......... | 510/441 |
| 6,245,732 B1 * | 6/2001 | Gallon et al. | ................ | 510/507 |
| 6,358,902 B1 * | 3/2002 | Angell et al. | ................ | 510/313 |
| 6,455,086 B1 | 9/2002 | Trinh et al. | | |
| 6,573,391 B1 * | 6/2003 | Eh et al. | ...................... | 549/267 |
| 6,602,410 B1 * | 8/2003 | Tanner et al. | ................ | 210/201 |
| 6,790,814 B1 * | 9/2004 | Marin et al. | ................. | 510/101 |
| 6,827,874 B1 * | 12/2004 | Souter et al. | ............... | 252/181 |
| 2002/0114730 A1 | 8/2002 | Jazzar | | |
| 2004/0126335 A1 * | 7/2004 | Faller et al. | .................. | 424/52 |

FOREIGN PATENT DOCUMENTS

| | | |
|---|---|---|
| EP | 0 602 891 A1 | 6/1994 |
| EP | 1 138 755 A2 | 10/2001 |
| WO | WO 02/00557 A2 | 1/2002 |

* cited by examiner

*Primary Examiner*—Joseph D. Anthony
(74) *Attorney, Agent, or Firm*—Dinsmore&Shohl, LLP

(57) ABSTRACT

A composition for disinfecting contaminated drinking water. The composition can include a disinfecting agent for disinfecting or sanitizing the water and a masking agent for masking or minimizing undesired characteristics of the disinfecting agent, such as taste and odor. The disinfecting agent can be a halogen-based disinfecting agent, such as a chlorine-based disinfecting agent. The masking agent can be a chlorine-compatible masking agent or flavorant, such as a citrus fruit derived flavor. The composition can also include a substrate. The substrate can be a clay, zeolite, water-soluble carrier, water-insoluble carrier, or mixtures thereof. The flavorant can be loaded onto the substrate. The composition can include other components, such as a primary coagulant, a coagulant aid, a bridging flocculant, a polymeric material, an alkali agent, an autocatalytic oxidant, and mixtures thereof.

36 Claims, 2 Drawing Sheets

WATER TREATMENT COMPOSITIONS WITH MASKING AGENT

FIELD OF THE INVENTION

The present invention relates to compositions, methods and kits for use in the purification of contaminated drinking water for purposes of rendering it potable. More particularly, the present invention relates to masking agents used to mask undesired taste or odor associated with the purification of the contaminated drinking water.

BACKGROUND TO THE INVENTION

There is a need for potable water in all areas of the world. In developed countries, water is purified and potable water is supplied on a large scale, typically by large national or multinational water management companies. This water is typically supplied directly to the consumers' homes in a potable form. However, in some parts of the world, for example in some rural areas of developing countries, many people either do not have a direct water supply to their homes and only have access to a non-potable communal water supply such as a village well, or it cannot be guaranteed that the water they do receive is potable. As a result, a considerable number of people die each year as the direct result of drinking contaminated water. Thus, there is a need for water purification kits and compositions that allow the consumer to purify their own water, which produces potable water in a fast and efficient manner.

Many water purification compositions available on the market to date consist of disinfectants that include chlorine or derivatives thereof. The amounts of such disinfectants needed to effectively purify water impacts the taste and odor of the resulting water. Flavorants can be added to change the taste and odor of the water. However, traditional flavorants used to change the taste and odor of the water significantly compromise the effectiveness of chlorine and chlorine derivatives disinfectants. Thus, there is a need to provide a water purification composition that disinfects contaminated water without imparting a taste or odor that consumers may find objectionable in the resulting potable water.

Another problem associated with the use of certain chlorine-based disinfectants, such as, for example, calcium hypochlorite, is that of product stability. In particular, it has been found that known compositions based on calcium hypochlorite can lose substantial disinfection efficacy when mixed with a flavorant. Thus, there is a need for disinfection compositions containing a flavorant having improved storage stability.

After disinfection of contaminated drinking water, a further problem includes maintaining residual disinfectant to protect the water from recontamination until such time as it is required for drinking, while at the same time providing drinking water of satisfactory taste. Thus, there is a need for compositions, methods and kits for purifying contaminated drinking water and for providing purified water having improved taste attributes for a period of time.

SUMMARY OF THE INVENTION

The present invention relates to compositions, methods and kits for use in the purification of contaminated drinking water for purposes of rendering it potable. More particularly, the present invention relates to masking agents used to mask undesired taste or odor associated with the purification of the contaminated drinking water.

According to one aspect of the invention, a composition for disinfecting water includes a disinfecting agent and a masking agent. The disinfecting agent is any compound that disinfects or sanitizes water. The masking agent is any compound that can mask or minimize undesired characteristics of the disinfecting agent, such as taste or odor.

In one embodiment, the disinfecting agent is halogen-based, and the masking agent is a citrus fruit derived flavor. Other types of disinfecting agents and compatible masking agents are also used. The composition can optionally include a substrate onto which the masking agent is loaded. The composition can also include other components, such as a primary coagulant, a coagulant aid, a bridging flocculant, a polymeric material, an alkali agent, an autocatalytic oxidant, and mixtures thereof.

The above summary is not intended to describe each disclosed embodiment or every implementation of the present invention. The detailed description which follows more particularly exemplifies these embodiments.

DESCRIPTION OF THE DRAWINGS

The invention may be more completely understood in consideration of the following detailed description of various embodiments of the invention in connection with the accompanying drawings, in which.

Figure 1:
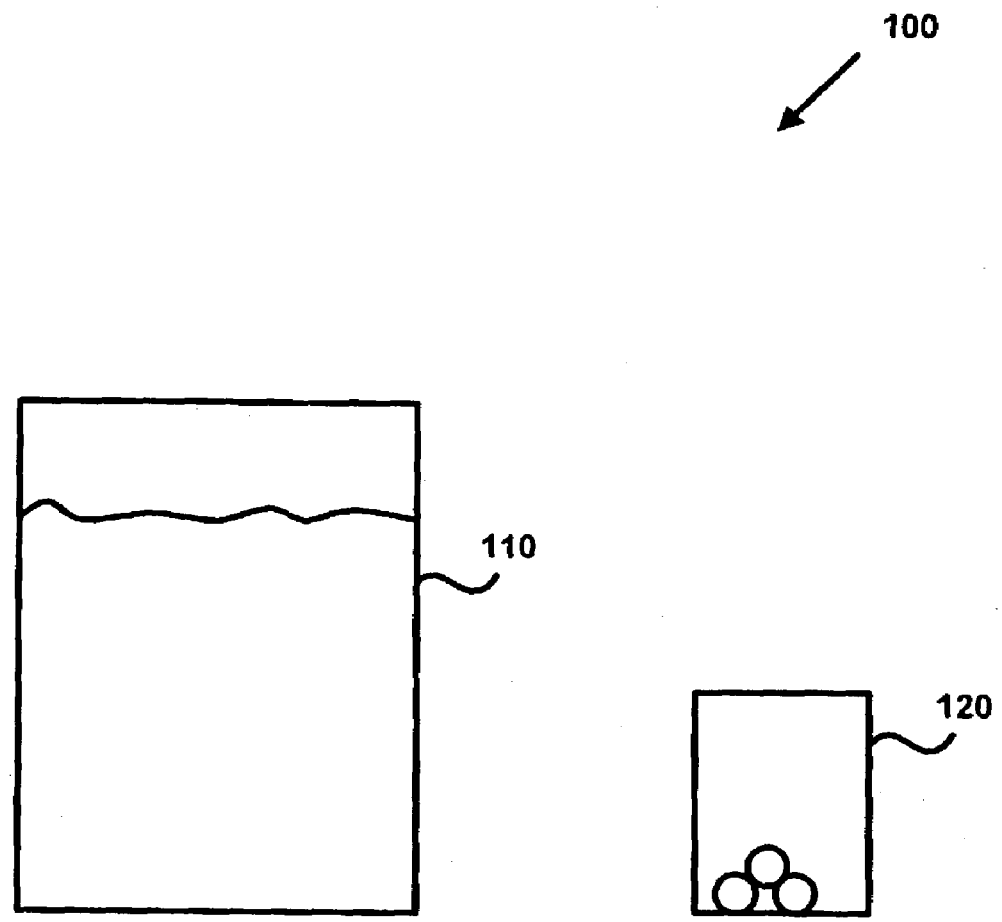
FIG. 1 is a schematic drawing of an example water purification kit made in accordance with an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

All documents cited are, in relevant part, incorporated herein by reference. The citation of any document is not to be construed as an admission that it is prior art with respect to the present invention.

Generally, the present invention relates to compositions, methods and kits for use in the purification of contaminated drinking water for purposes of rendering it potable or safer to drink. More particularly, the present invention relates to masking agents used to mask undesired taste or odor associated with the purification of the contaminated drinking water.

Compositions including disinfecting agents to purify water can leave an undesirable taste or odor. For example, halogen-based disinfecting agents, such as chlorine, used to purify water can leave an unpleasant taste and odor associated with the chlorine. The present invention described herein generally relates to masking agents that are used in conjunction with disinfecting agents to minimize the taste and odor associated with the disinfecting agents.

The masking agent may be loaded on a substrate. This loading may be advantageous to assist in the delivery of the masking agent, while at the same time minimizing any negative interaction between the masking agent and the disinfecting agent.

The example compositions disclosed herein can, but need not, further include one or more of the following components: a primary coagulant, a coagulant aid, a bridging flocculant, a polymeric material, an alkali agent, and an autocatalytic oxidant.

The various components of the example compositions are described in further detail below.

I. Definitions

As used herein, the term "activated" refers to a substance that has been treated so that the substance will catalyse chemical or physical change more rapidly and/or completely. This is typically achieved by drying the materials.

As used herein, the term "activity loss" refers to the loss, degradation, or impairment of disinfecting, sanitizing, purifying, biocidal and/or anti-microbial properties.

As used herein, the term "aperture" refers to the gap through which a molecule must fit to access void spaces within a given substrate. These include platelet gaps or pores of varying sizes.

As used herein, the terms "chlorine" and "chlorine derivatives" and "chlorine based" refer to the nonmetallic halogen element of atomic number 17, as well as derivatives and synthetic analogs thereof, including, but not limited to, chlorine dioxide, chloramine, hypochlorites including calcium hypochlorite and sodium hypochlorite, and isocyanurates.

As used herein, the term "chlorine-compatible" refers to an agent that does not substantially degrade the chlorine or otherwise substantially interfere with the disinfecting, sanitizing, purifying, biocidal and/or anti-microbial properties of chlorine.

As used herein, the term "citrus fruit" or "citrus fruit derived" or "citrus fruit extract" refers to fruits including bergamot, grapefruit, lemon, lime, orange, and tangerine, as well as to a flavor-component thereof, and/or a synthetic analog thereof, and/or an extract thereof.

As used herein, the term "compatible" refers to a species that does not substantially degrade or otherwise interfere with the function(s) of the species with which the species is said to be "compatible" with.

As used herein, the term "control sample" refers to a sample of the composition that is free from masking agents.

As used herein, the terms "degrade" and "degradation" refer to a reduction in the efficacy of a particular substance for a particular purpose.

As used herein, the term "disinfecting agent" refers to any compound that has disinfecting activity, in that the disinfecting agent acts to disinfect, sanitize, purify, and/or otherwise place water in a more potable form, including biocidal and anti-microbial agents.

As used herein, the terms "flavor," "flavorant," and "flavor component" refer to one or more substances, such as, for example and without limitation, a citrus fruit, that are used to mask an undesired taste and/or odor or to impart a desired taste and/or odor.

As used herein, the term "free-moisture content" refers to water, that is freely available as measured either by Karl Fisher methods or by loss on drying at 150° C.

As used herein, the term "halogen-based" refers to an agent that does not substantially interfere with the disinfecting, sanitizing, purifying, biocidal and/or anti-microbial properties of the halogen species.

As used herein, the term "halogen-compatible" refers to an agent that does not substantially degrade the halogen species or otherwise substantially interfere with the disinfecting, sanitizing, purifying, biocidal and/or anti-microbial properties of the halogen species.

As used herein, the terms "loading" and "loaded" refer to releasably binding a component to a substrate using a method such as, for example, spraying, spray drying, or otherwise encapsulating, retaining, or isolating a component.

As used herein, the term "masking agent" refers to a composition used to mask an undesired taste and/or odor.

As used herein, the phrase "meaningful 1-day residual chlorine content" refers to a chlorine level of at least 0.1 ppm, capable of protecting stored water from viral and bacterial recontamination.

As used herein, the term "moisture sink" refers to a substance that absorbs available free water.

As used herein, the phrase "odor detection threshold" refers to the level at which at least 50% of individuals can smell a disinfecting agent in water (assuming a minimum panel size of 10 individuals).

As used herein, the term "shelf life" refers to a length of time a composition retains its desired characteristics.

As used herein, the term "substrate" refers to a substance or composition onto which a different substance or material can be coated, layered, or otherwise releasably deposited.

As used herein, the phrase "taste detection threshold" refers to the level at which at least 50% of individuals can taste a disinfecting agent in water (assuming a minimum panel size of 10 individuals).

II. Disinfecting Agent and Related Components

The example compositions illustrated herein preferably include a disinfecting agent. The disinfecting agent can include any compound that disinfects or sanitizes water. The disinfecting agent can be inorganic such as, for example, silver salts, colloidal silver, nanosilver, ozone, chlorine dioxide, chlorine, sodium hypochlorite, calcium hypochlorite, chloramines, organic sources of chlorine such as isocyanurates or Halosource, iodine, or sources of iodine, such as polyiodide resins. The disinfecting agent can also be organic, such as a quaternary ammonium compound.

In the preferred embodiments, the disinfecting agent is a halogen-based disinfecting agent such as chlorine, or a derivative thereof, including, but not limited to, chlorine dioxide, calcium hypochlorite, sodium hypochlorite, organic sources of chlorine such as isocyanurates or chloramine. Preferred disinfecting agents include inorganic chlorine based disinfectants, wherein the chlorine is in a formal oxidation state that is not minus one, preferably above minus one. Preferred sources of chlorine include hypochlorites (including calcium hypochlorite) and organic sources of chlorine such as isocyanurates.

The disinfecting agent is preferably used in a controlled, delayed, sustained or slow release form (herein referred to as "delayed release"). Such delayed release can be accomplished by blending or coating the disinfecting agent with, for example, a poorly water-soluble or hydrophobic material, or providing a coating of sufficient thickness that the kinetics of dissolution of the coating provide delayed release. Poorly water-soluble or hydrophobic materials include waxes, paraffins, silicas, zeolites, clays, polymeric resins, celluloses, cross-linked polymers, insoluble salts such as calcium carbonate, etc. The coating material can be applied by agglomeration in, for example, pan, rotary drum and vertical blenders, or by spray atomization. Other ways to provide delayed release include mechanical methods for altering the physical properties of the disinfecting agent including, for example, compaction, granulation methods for altering the particle size distribution of the disinfecting agent, etc.

In one illustrated embodiment, a particulate disinfecting agent, preferably calcium hypochlorite, is used, having a particle size distribution such that at least about 50%, about 75%, or about 90% by weight is retained on a 210 μm (Tyler 65 mesh) screen, a 425 μm (35 mesh) screen, a 600 μm (28 mesh) screen, a 710 μm (24 mesh) screen, a 850 μm (20 mesh) screen, or a 1000 μm (16 mesh) screen. In order to minimize random sampling variance in the final unit dose composition, it is also preferable that the particulate disinfecting agent has a particle size distribution such that at least about 50% or about 75% or about 100% by weight thereof passes through a 2000 μm (9 mesh) screen or through a 1400 μm (12 mesh) screen.

The example composition illustrated herein preferably includes (by weight) from about 0.01%, about 0.1%, about 0.2%, about 0.5%, about 0.7%, about 1.0%, about 1.2%, or about 1.5%, and preferably to about 20%, about 10%, about 5%, about 4%, or about 2.5% disinfecting agent.

The example compositions can, but need not, also include other components in addition to the disinfecting agent. For example, the example compositions preferably include a primary coagulant. Primary coagulants suitable for use herein include water-soluble inorganic salts and mixtures thereof. In the illustrated embodiments, the compositions include an inorganic metal salt selected from the group consisting of iron sulphate, iron chloride, manganese sulphate, manganese chloride, copper sulphate, copper chloride, aluminium sulphate, aluminium chloride, poly-variations thereof, and combinations thereof. The inorganic metal salt can act as a coagulant and interacts with charged water-soluble impurities in such a manner to neutralize the charge of the water-soluble impurity to form a water-insoluble impurity, usually to form a water-insoluble salt of the impurity, which precipitates out of solution.

The example composition illustrated herein preferably includes (by weight) from about 1%, about 5%, about 10%, about 15%, about 20%, or about 25%, and preferably to about 50% or about 40% inorganic salt selected from the group consisting of iron sulphate, iron chloride, manganese sulphate, manganese chloride, copper sulphate, copper chloride, aluminium sulphate, aluminium chloride, poly-variations thereof, and combinations thereof.

The example compositions can also include a water-insoluble silicate such as clays, zeolites, and mixtures thereof, to function as a water-insoluble coagulant aid. For example, clays act as a seed particle onto which water-insoluble impurities can aggregate to form flocs. The presence of clay in the composition improves the rate of floc formation and allows the formation of larger flocs compared to when clay is absent from the composition herein. The clay may also act as a swelling agent, and if the composition herein is in the form of a tablet, the clay improves the rate at which the tablet disintegrates on contact with water by swelling upon contact with water so that the components of the tablet are pushed apart by the swollen clay particles. The clay can also act as a desiccant within the tablet. The clay can also act as a cationic exchange agent to remove metal ions from the water and the clay can also remove color, heavy metals and some organic material from water by adsorption. Aluminosilicates can be used herein in place of, or in addition to, clay. The aluminosilicate can act as a cationic exchange agent to remove metal ions from water, and can also act as a seed particle to enhance floc formation and as dessicant for enhancing disinfectant stability.

More specifics on example water-insoluble silicates that can be used are provided in section IV, supra, in which examples of substrates including water-insoluble silicates are provided.

The example compositions can also include other coagulant aids. In the examples shown, the coagulant aid includes polymeric materials that have an amine group and which are therefore cationic in nature. The coagulant aid assists in the coagulation and flocculation processes and, in particular can, in conjunction with the primary coagulant, aid particle adherence and the aggregation of water-insoluble particles into larger water-insoluble aggregated complexes known as flocs. The coagulant aid can also adsorb or coagulate oils, fats and other organic or inorganic matter, and can sequester heavy metal ions. Preferably, the coagulant aid is substantially water-insoluble.

The example composition preferably includes (by weight) from about 0.1%, about 0.5%, about 1%, about 1.5%, about 2%, or about 2.5%, and preferably to about 50%, about 40%, about 30%, about 20%, about 10%, about 5%, or about 4% coagulant aid.

The example compositions can also include a bridging flocculant. Preferably, the bridging flocculant is substantially water-soluble at in-use concentrations and has a weight average molecular weight of at least about 100,000, preferably more than about 1,500,000 or at least about 2,000,000. The bridging flocculant is selected on the basis that it can act as flocculent and cause the aggregation of water-insoluble particles into larger water-insoluble aggregated complexes known as flocs. The bridging flocculant is preferably of greater molecular weight than the coagulant aid and preferably does not include an amine group. In the example embodiments, the bridging flocculant includes an amide group. Preferably, the bridging flocculant is a polyacrylamide. Typical anionic and nonionic polyacrylamides for use herein are those from the Magnafloc® range supplied by Ciba Specialty Chemicals.

Preferably, the example compositions can include (by weight) from about 0.1%, about 0.2%, about 0.5%, or about 1%, and preferably to about 30%, about 20%, about 10%, about 5%, or about 3% bridging flocculant.

The illustrated compositions can also include another polymeric material. This example polymeric material preferably does not contain an amine group and is substantially water insoluble. Thus, the polymeric material is distinguishable from the coagulant aid and the bridging flocculant. The polymeric material acts as a seed particle to enhance floc formation. Preferably, the polymeric material includes cellulose, and preferably, the polymeric material is an unmodified cellulose. Preferably, the polymeric material includes powdered cellulose.

The example compositions illustrated herein preferably include (by weight) from about 1%, about 5%, about 10%, about 15%, about 20%, or about 25%, and preferably to about 80%, about 50%, or about 35% polymeric material.

The example compositions illustrated herein can also include an alkali agent. The alkali agent can be any compound that gives alkalinity when contacted to water. The alkali agent for use herein is preferably not a polymeric material. The compositions herein preferably include an amount of alkali agent such that, when the composition herein is contacted to water to form a solution, the solution has a pH of from about 5 to about 8, preferably from about 6 to about 7.

Preferred alkali agents are selected from the group consisting of sodium carbonate, sodium bicarbonate, sodium hydroxide, sodium oxide, calcium carbonate, calcium bicarbonate, calcium hydroxide, calcium oxide, potassium carbonate, potassium bicarbonate, potassium hydroxide, potassium oxide and combinations thereof. Particular alkali agents that are a source of carbonate when contacted to water, for example sodium carbonate or sodium bicarbonate, are preferred. Preferred, especially in compositions containing calcium hypochlorite as disinfecting agent, are alkalis that can also act as moisture sinks, such as anhydrous sodium carbonate.

The example compositions illustrated herein typically include (by weight) from about 1% to about 50%, preferably from about 10%, about 15%, about 20%, or about 25%, and preferably to about 45%, about 40%, or about 35%, alkali agent.

In a preferred embodiment, the example compositions also include an oxidant system. The function of the oxidant system is to oxidise the soluble manganese (Mn(II)) content of the drinking water and coagulant to colloidal manganese dioxide to the fullest possible extent within the natural timeframe of the coagulation/flocculation reaction. Because the coagulation/flocculation systems of the compositions of the invention can be highly active, typically giving at least about 80% reduction in the organic matter content of the drinking water within about 30 seconds and substantially complete flocculation within about 5 minutes, considerable demands are imposed on the oxidant system.

Preferred from the viewpoint of providing rapid and effective oxidation of soluble manganese and optimum control of manganese-associated post-flocculation discoloration are oxidant systems selected from the group consisting of autocatalytic oxidants, combinations of oxidants and oxidation catalysts, and mixtures thereof. The oxidants utilized herein should have an oxidation-reduction potential in excess of the $MnO_2/Mn(II)$ system under the conditions of use and preferably having a standard oxidation-reduction potential of at least about 1.23 V. In one embodiment, when incorporated in the compositions of the invention, an amount of the oxidant system sufficient to provide about 200 ppb of autocatalytic oxidant or oxidation catalyst should preferably reduce the soluble manganese concentration of deionised water containing about 150 ppb of soluble manganese by at least about 50% or about 60% in one minute and by at least about 60% or about 70% in about five minutes, soluble manganese concentration being measured by atomic absorption spectroscopy and the test being run at ambient temperature (about 20° C.). Autocatalytic oxidants and oxidation catalysts preferred for use herein are transition metal-based, especially preferred being those of Groups V, VI, VII and VIII of the Periodic Table such as Mn, Co, V, Mo and Ru, and mixtures thereof. Highly preferred autocatalytic oxidants for use herein include the manganates and especially potassium permanganate. Oxidation catalysts suitable for use herein include manganese dioxide itself and the manganese and cobalt catalysts described for example in PCT Application Ser. No. WO 97/00311, U.S. Pat. No. 5,246,612, U.S. Pat. No. 4,810,410, European Patent Application No. 0408131, and U.S. Pat. No. 5,244,594. Oxidants suitable for use in combination with the oxidation catalysts, or indeed with the autocatalytic oxidants, include the chlorine-based disinfectants, the combination of chlorine-based disinfectants and autocatalytic oxidants being especially beneficial from the viewpoint of providing rapid and effective oxidation of soluble manganese within the timeframe of the coagulation/flocculation reaction.

Preferably the compositions herein comprise from about 0.001% to about 0.15%, about 0.01% to about 0.1%, or about 0.01% to about 0.05% by weight of the autocatalytic oxidant, oxidation catalyst or mixture thereof.

Water treatment chemicals such as ferrous and ferric sulphate are typically manufactured from source materials having a high soluble manganese content that is retained to varying degrees in the final commercial product. A small proportion of soluble manganese in the coagulant can be desirable from two reasons. First, it promotes the oxidation reaction leading to lower final levels of soluble manganese and reduced post-flocculation discoloration, especially in highly contaminated water conditions, enabling for example water containing as much as about 200 to about 300 ppb of soluble manganese to be reduced after flocculation to as little as about 50 ppb or lower in some instances. Second, it provides a compensating load under conditions of low soluble manganese contamination, thereby enabling the post-flocculation level of the autocatalytic oxidant to be kept to a minimum. This can be particularly important in the case of oxidant systems based on potassium permanganate that can lead to the treated water developing a pink hue if the oxidant is present in excessive amounts.

The compositions disclosed herein preferably include as part of the coagulant or otherwise from about 0.001% to about 0.2%, about 0.002% to about 0.1%, or about 0.003% to about 0.05% of manganese in the form of Mn(II). The weight ratio of Mn(II) to the autocatalytic oxidant such as potassium permanganate, on the other hand, preferably lies in the range from about 1:10 to about 10:1, 1:5 to about 5:1, or about 1:4 to about 2:1.

The example compositions illustrated herein preferably also include a substrate, as described in more detail in section IV supra.

The disinfecting agent and related components used in the embodiments illustrated herein are further described and defined in PCT Application Serial No. WO 02/00557, entitled "Water Treatment Compositions" and filed on Jun. 21, 2001, and PCT Application Serial No. WO 03/011769 entitled "Water Treatment Compositions" and filed on July 26, 2002, both being assigned to the same assignee as the present invention.

III. Masking Agent

Masking agents (sometimes referred to herein as flavorants or flavoring agents) suitable for use herein are preferably chlorine-compatible so that the masking agents do not substantially degrade or inhibit a disinfecting agent including chlorine.

There are multiple components of flavoring agents that can negatively impact the biocidal effectiveness of chlorine. For instance, reactive organic species such as aldehydes, that form part of the chemical makeup of most flavorants, can degrade the chlorine. Also, many flavorants contain reactive alkenes such as d-limonene that can degrade the chlorine. Additionally when d-limonene is oxidized by some oxidants, the resultant derivatives produced can be undesirable as a possible sensitizer.

For these reasons, it is important to "lock away" the reactive aspects of the flavor while the product is stored in its package before use. This can be accomplished, for example, by binding the masking agent to a substrate, as described further below.

The example masking agents used herein can mask the taste and odor of chlorine in the treated drinking water while preserving the effects of the disinfecting agent, such as chlorine. In the illustrated embodiments, the masking agent includes a citrus fruit derived flavor. For example, the masking agent can include a citrus fruit extract selected from the group consisting of bergamot, lemon, lime, orange, tangerine, grapefruit, and mixtures thereof.

The masking agent can also include a substantially terpene-free (also referred to as "terpeneless") citrus fruit derived flavor. A terpene-free masking agent is substantially free from terpene components (i.e., unsaturated hydrocarbons based on the isoprene unit $C_5H_8$) that may produce undesired effects. A terpene-free masking agent is defined as a masking agent containing less than about 10% or about 5% d-limonene.

Other masking agents or components thereof, such as, for example, chocolate, vanilla, honey maple, and other non-citrus fruits, can also be used. Additional flavor types include precursors to or the products of the heating or enzymolysis of natural matter (e.g., carbohydrates, proteins, amino acids, lipids, hydrolyzed proteins, autolyzed yeast, ribonucleotides, ascorbic acid, thiamine). For example, compounds, including extracts or synthetic analogs thereof, isolated from the flavors and flavorings that characterize, reinforce, or resemble any of the noted flavors, are listed below. The following list is provided by way of example only:

Chocolate—e.g., 5-methyl-2-phenyl-2-hexenal vanillin, ethyl vanillin, cocoa and extracts/distillates from cocoa, linalool, ethyl maltol, maltol, diacetyl, acetyl propionyl, C4–C16 alkanoic acids, 2,3-dimethyl-3-(2H)-furanone, 3-methyl-butanal, alkyl substituted pyrazines, 4-methyl-5-vinylthiazole, 2,4-dimethyl-5-vinylthiazole, trimethylthiazole, 5-ethyl-2,4-dimethylthiazole, 2,5-dimethylthiazole, isopropyl phenylhexenal, 2,6-dimethylpyrazine, tetramethylpyrazine, 2-ethyl-3,6-dimethylpyrazine, methyl cyclopentenolone, 2-isopropyl-3-methoxypyrazine, 2-ethyl-5methylpyrazine, 2,5-dimethylpyrazine, 2,5-dimehtyl-3-ethylpyrazine, 2,6-dietyhpyrazine, 4-methyl-5-vinylthiazole, 2,4-dimethyl-5-vinylthiazole, trimethylthiazole, 5-ethyl-2,4-dimethylthiazole, 2,5-dimethylthiazole, isopropyl phenylhexenal, 2,6-dimethylpyrazine, tetramethylpyrazine, 2-ethyl-3,6-dimethylpyrazine, methyl cyclopentenolone, 2-isopropyl-3-methoxypyrazine, 2-ethyl-5methylpyrazine, 2,5-dimethylpyrazine, 2,5-dimehtyl-3-ethylpyrazine, 2,6-dietyhpyrazine, 4-hydroxy-2,5-dimethyl-3(2H)-furanone, ascorbic acid, 2-methoxy-3-methylpyrazine, 2-acetyl pyridine, trimethyloxazole, 2-methyl-2butenal, amino acids (especially alanine, cysteine, cystine, glutamine, glutamic acid and its salts, glycine, isoleucine, leucine, lysine, methionine, phenylalanine, proline, serine, threonine, valine), vitamins (especially ascorbic acid, and thiamine), whey, milk powder, fructose, glucose, arabinose, xylose, lactose, methyl glyoxal;

Vanilla—e.g., vanillin, ethyl vanillin, maltol, ethyl maltol, Furaneol, heliotropine, nutmeg, extracts and distillates of vanilla, benzaldehyde;

Vegetable (corn, rice, celery, cucumber, horseradish, shallot, soybeans, tomato)—e.g., isobutyl thiazole, dimethyl sulfide, dimethyl disulfide, dimethyl trisulfide, allyl disulfide, butylidene phthallide, propylidene phthalide, methyl cyclopentenolone, hexanal, E-2-hexenal, Z-3-hexenol, allyl isothiocyanate, beta-ionone, alpha-ionone, methyl octine carbonate, methyl heptene carbobate, Z-6-nonenal, Z-6-nonenyl acetate, 2-methyl butylacetate, Z-6-nonenal, Z-6-nonenol, 2,6-nonadienal, 2,6-nonadienol, 1-octen-3-ol, extracts-powders-distillates of vegetable;

Citrus fruits (especially orange, lemon, lime, tangerine, clementine, grapefruit, kumquat, kalamansi, mandarine)—e.g., limonene, aliphatic aldehydes C2–C12), valencene, alpha and beta-sinensal, linalool, citronellol, citronellal, neryl acetate, geranyl acetate, geraniol, neral, geranial, dimethyl anthranilate, acetaldehyde, methyl and ethyl C2–C12 esters, perilla aldehyde;

Non-citrus fruits (especially apple, banana, cherry, fruit punch, apricot, peach, strawberry, blackberry, current, melon, grape, raspberry, kiwi, pineapple, mango, passionfruit, guava, papaya, pear, cupuacu, coconut)— e.g., Furaneol, ethyl-2-hydroxybutyrate, ethyl-2-methyl-4-pentanoate, 2-methyl-2-pentenoic acid, ocimene, acetaldehyde, ethyl acetate, ethyl butyrate, ethyl-2-methylbutyrate, Ethyl Maltol, Maltol, 2,3-butanedione, vanillin, benzaldehyde, isoamyl acetate, linalool, linalyl acetate, isobutyl butenoate, 2,3-dimethyl-3-(2H)furanone, p-mentha-8-thio-3-one, gamma-nonalactone, gamma-decalactone, gamma-dodecalactone, gamma-undecalactone, delta-decalactone, delta-dodecalactone, dimethyl sulfide, dimethyl disulfide, methyl anthranilate, E-2,Z-6-nonaldienal, E-2-hexenal, Z-3-hexenol, hexanol, hexanal, methoxyisobutylpyrazine, benzyl acetate, citral, octanal, decanal, alpha-terpineol, nonanal, 5-ethyl-3-hydroxy-4-methylfuranone, 2,6-dimethyl-5-heptenal, allyl caproate, alpha-ionone, beta-ionone, damascenone, damascone, allyl isothiocyanate, ethyl 2,4-decadienoate, dimethyl benzyl carbinyl isobutyrate, p-hydroxyphenylbutanone, methyl salicylate, ethyl vanillin, neryl acetate, geranyl acetate, geraniol, nerol, isobutyl acetate, butyric acid, caproic acid, capric acid, myristic acid, lauric acid, propionic acid valeric acid, isovaleric acid, palmitic acid, butanol, octanol, decanol, ethyl acetoacetate, ethyl propionate, ethyl isovalerate, ethyl-3-methylpropionate, allyl cyclohexanpropionate, Z-3-hexenyl acetate, phenyl acetaldehyde, phenylethanol, phenyl acetic acid, alpha-amyl cinnamic aldehyde, menthol, gamma-octalactone, oxathiane, methylthiobutyrate, 6-methyl coumarin, 4-hydroxy-5-methyl-(2H)-furanone, 1-p-mentha-8-thiol, isoamyl alcohol, n-butanol, acetic acid, methyl eugenol, isoeugenol, cis-jasmone, p-isopropylbenzaldehyde, alpha and beta-pinene, gamma-terpinene, methyl cinnamate, butyl acetate, 2 and 3 methyl butanals, benzyl alcohol, 2-methyl-2-butenal, methyl cyclopentenolone,. 2-methyl pentenoic acid, 5-methyl-4-hydroxy-3(2H)furanone, 2,5-dimethyl-4-methoxy-3(2H)furanone, methyl octine carbonate, methyl heptene carbobate, Z-6-nonenal, Z-6-nonenyl acetate, 2-methyl butylacetate, 1-(E,Z)-3,5-undecatriene, 2,5-dimethyl-4-hydroxy-3(2H)furanone, 2,6-dimethyl-4-methoxy-3-(2H)furanone;

Honey—e.g., phenyl acetaldehyde, phenylethanol, phenyl acetic acid, alpha-amyl cinnamic aldehyde;

Maple—e.g., methyl cyclopentenolone, vanillin, ethyl vanillin, Furaneol, 3-hydroxy-4,5-dimethyl-2-(5H) furanone;

Coffee—e.g., alpha furfuryl mercaptan, furfuryl thioacetate, furfural, methyl furfural, alkyl pyrazines, 2-acetyl furan, 2,2-(dithiodimethylene)difuran;

Tea—e.g., E-2-hexenal, Z-3hexenol, hexanal, hexanol, linalool, geraniol, nerolidol, beta-ionone, alpha-ionone, damascenone, damascone, linalool oxide, Z-jasmone, methyl jasmonate;

Herbs and Spices (especially cassia, juniperberry, cinnamon, cardamom, mace, thyme, caraway, cumin, clove, nutmeg anise, fennel, allspice, dill, pepper, basil, ginger, rosemary, sage, bell pepper, green pepper, red pepper, oregano)—e.g., cinnamic aldehyde, eugenol, estragol, methoxy isobutyl pyrazine, cumin aldehyde, anethole, methyl salocylate; and Mints (especially peppermint, spearmint, cornmint)—emifmenthol, I-carvone.

As described further below, the masking agent can be delivered to simultaneously with the disinfecting agent, or can be delivered separately. For example, in one embodiment, the masking agent can be added as a premix with water-swellable smectite-type clay. The premix preferably includes a level of masking agent sufficient to provide strong intra-laminar adsorption based on both clay-flavorant and flavorant-flavorant interactions.

The example compositions illustrated herein preferably include (by weight) about 0.5% to about 20%, about 1% to about 15%, or about 2% to about 10% masking agent. The diluted compositions (i.e. the treated water) disclosed herein preferably include about 10 ppb to about 2000 ppb, about 20 ppb to about 300 ppb, about 25 ppb to about 200 ppb, about 25 ppb to about 150 ppb, or about 50 ppb to about 150 ppb masking agent at a temperature range of about 200 to about 30° C.

As previously noted, the example masking agents provided herein function to reduce taste and odor associated with the disinfecting agent. Individuals may find the taste and/or odor of chlorine in water aesthetically unacceptable, especially at levels of about 0.5 ppm and above. The level at which an individual can smell chlorine is the chlorine odor detection threshold and the level at which a consumer can taste chlorine is the taste detection threshold. Addition of a suitable masking agent alters the level at which an individual can either taste chlorine or smell chlorine or preferably both.

The odor detection threshold is defined as the level at which at least about 50% of individuals can smell chlorine in the water. External factors such as individual sensitivities and the temperature of the water will affect this threshold. For the experiments to measure the odor detection threshold described herein, water samples of a fixed volume (1 liter) were kept at a fixed temperature (20° C.), with a fixed headspace (120 ml) and a panel of trained perfumers and untrained individuals were asked to smell and indicate whether chlorine was present. Control samples containing 0, about 0.5, about 1, about 2, and about 5 ppm of chlorine were compared to samples containing the same levels of chlorine but low levels of the masking agent. The test panel included 18 individuals. While about 60% of the panelists could detect chlorine at about 0.5 ppm and 100% at about 1 ppm in the control samples, in the presence of the masking agent, less than about 50% could detect chlorine at levels up to about 2 ppm, and, at about 5 ppm, about 10% of panelists could still not detect chlorine.

The taste detection threshold is defined as the level at which at least 50% of individuals can taste chlorine in water. External factors such as individual sensitivities and the temperature of the water will affect this threshold. For the experiments to measure the taste detection threshold described herein, water samples of fixed volume (about 50 ml) were kept at a fixed temperature (about 20° C.), in a fixed volume cup (about 200 ml). Individuals were asked to taste and indicate whether chlorine was present. Control samples containing 0, about 1, about 2, and about 5 ppm of free chlorine were compared to samples containing the same levels of chlorine but also low levels of the masking agent.

The test panel included 13 individuals. While about 78% of the panelists could detect chlorine at about 1 ppm and 100% at about 5 ppm in the control samples, in the presence of the masking agent less than about 50% could detect chlorine at levels up to about 2 ppm and, about 5 ppm, about 22% of the panelists could still not detect chlorine.

In preferred embodiments, the chlorine odor detection threshold is increased to at least about 0.2 ppm, about 0.5 ppm, about 1 ppm, or about 2 ppm. In other preferred embodiments, the chlorine taste detection threshold is increased to at least about 0.2 ppm, about 0.5 ppm, about 1 ppm, or about 2 ppm. In most preferred embodiments, both the odor and taste detection thresholds are increased to at least about 0.2 ppm, about 0.5 ppm, about 1 ppm, or about 2 ppm.

IV. Substrate

The compositions illustrated herein can include a suitable substrate selected from clays, aluminosilicates, other water-insoluble carriers, water-soluble carriers, and mixtures thereof.

The example substrate preferably has an ideal binding energy that accounts for the interplay between surface area, aperture size, hydrophilic/hydrophobic nature, and surface topography. The substrate preferably binds a predetermined amount of flavorant prior to dilution and then releases a predetermined amount of flavorant upon dilution into contaminated water.

The masking agents of the illustrated embodiments are preferably oils (e.g., citrus extracts), and thus are liquids that are incorporated into a dry solid matrix. This can be achieved by binding the flavor to an inert solid substrate. The energy by which the flavorant is bound to the substrate is the "binding energy" and can be described as:

$$Fv(g) + IS(s) \rightarrow Fv\text{---}IS(s) \quad \Delta G_{be} = \text{binding energy}$$

This process must be more favorable than that of the flavor molecules self-associating to reform the liquid oil:

$$Fv(g) \rightarrow Fv(l) \quad \Delta G_c = \text{condensation energy}$$

In other words, for the carrier to be effective, $\Delta G_{be}$ must be less than $\Delta G_c$. This is the case, for example, for clays and zeolites, but not, for example, for various grades of sodium carbonate.

A strong binding energy can help to ensure that: (1) the flavor is easy to load and incorporate into the matrix; and (2) the flavor is strongly bound within the package such that it is not rapidly degraded or acts as a solvent/medium for other species to degrade. In particular, interactions with the hypochlorite may be important.

However, for the illustrated embodiments, not only the binding energy is important. It is also important that the masking agent release into the solution, which is a function of binding energy:

$$Fv\text{---}Is(s) + H_2O(l) \rightarrow Fv(aq) + IS\text{---}H_2O(s)$$
$$\Delta G_r = \text{release energy}$$

For this release process to occur, $\Delta G_r$ must be less than zero (0). To favor this process, it is preferable that the substrate is hydrophilic.

The binding energy, $\Delta G_{be}$, and the release energy, $\Delta G_r$, are affected by several factors, including:

1. Surface Area and Pore Size of Inert Substrate Versus % Loading.

High surface area is usually preferred for strong adsorption.

Thus, high surface area and low loading is usually advantageous because there is a greater chance of strong adsorption to thermodynamically most favorable sites for substrate-flavor interaction.

Pores that are sufficiently wide to allow binding of more than one flavor molecule within in a pore can be advantageous as enthalpically beneficial flavor-flavor interactions can supplement the flavor—substrate interactions. To drive these flavor-flavor interactions high loadings are favored.

2. Chemical Nature of Substrate.

The flavor is preferably hydrophobic, so that a hydrophobic structure (in the case of zeolites or clays this means a high Si:Al ratio or some sort of post-treatment, e.g., silylation or controlled acid washing) is preferred to obtain a high binding energy.

Overall, competing mechanisms operate between hydrophobicity and hydrophilicity such that, if the substrate is too hydrophobic, while it gives excellent binding in the premix it may not release sufficiently upon dilution.

Consequently, some embodiments, the hydrophilic species are favored. Preferably the loading substrate should be dry and activated such that there are surfaces onto which the flavor can bind without substantial competition from water.

3. Surface Topography.

Surface topography of the substrate is also important. Rougher surfaces may adsorb more strongly, as 'holes' of suitable size to strongly adsorb molecules are more prevalent.

In addition to thermodynamic considerations, it may also be important that the kinetics of binding and release are sufficiently rapid.

The following attributes are therefore desirable:

(i) For Binding

Accessibility of the surface area does not affect the theoretical binding energy, but does affect the 'practicality of adsorption'—i.e., whether the kinetics are fast enough to actually observe the adsorption. Accessibility is determined primarily by aperture size of the inert carrier. A high aperture size, such as those seen in clays and some zeolites, can be kinetically advantageous to ensure that the flavorant can access the sites to which the binding will occur. Preferred flavors include small organic molecules that may only access gaps of greater than or equal to about 5 Å. Most molecules cannot access gaps in the less than about 5 Å range, so preferred carriers will have platelet gaps or pores of at least these sizes. Aperture sizes from about 4 Å to about 100 Å, about 4 Å to about 50 Å, or about 5 Å to about 25 Å are preferred.

(ii) For Release on Contact with Water.

Again accessibility of the pores is key such that large aperture sizes (greater than or equal to about 5 Å) are preferred.

As water is typically smaller than the flavor molecules then in practice this is not a limiting factor.

Additionally it may be preferred that the chosen substrate can act as a swelling agent such that, upon contact with water; it swells so that the flavorant is released rapidly. Such rapid release of at least part of the flavor is highly desired to ensure odor masking of the disinfectant, especially chlorine, during the water purification process.

The optimum substrate preferably balances the correct thermodynamics (sufficient binding energy to bind the flavor and protect it on storage with a strong enough release energy that the flavor is released upon exposure to the bulk/liquid water it is used to treat) with the correct kinetics (rapid adsorption of flavor and rapid release of at least part of said flavor on contact with water).

For example, Zeolite Y (hydrophobic—pore size ca. about 8 Å) provides high binding energies, but when added to the water, the flavor may not release sufficiently, as either it is thermodynamically disadvantageous (i.e., the flavor is too tightly held and the hydration enthalpy of the zeolite cannot overcome this binding such that $\Delta G_r$ is greater than zero (0)) or it is kinetically disadvantageous (low aperture size makes for slow release of flavor) Therefore, release may not occur in a useful (e.g., less than about 30 minutes) timeframe.

In another example, more hydrophilic clays can satisfy both conditions (i.e., bind the flavors sufficiently strongly in the package, but then release it on contact with water).

Preferably, at least about 20% of the masking agent is released into the water within about two (2), about 50% of the masking agent is released into the water within about 10 minutes, or about 70% of the masking agent is released into the water within about five (5) minutes. In another embodiment, at least about 20% of the masking agent is released into the water within about 15 minutes.

Examples of preferred substrates are detailed below.

A. Clays

The clay used is preferably a smectite clay, a dioctahedral smectite clay such as montmorillonite clay, or a trioctahedral smectite clay such as hectorite clay. Those clays found in bentonite clay deposits are also preferred. Preferred clays for use herein include laponite, hectorite, montmorillonite, nontronite, saponite, volkonsite, sauconite, beidellite, allevarlite, illite, halloysite, attapulgite, and like clays supplied by Gimpex Ltd. of Tamil Nadu, India, Laviosa Chimica Mineraria of Livorno, Italy, ABI of Illinois, USA, Atta Clay (Pty) Ltd. of Isando, South Africa, CSM of Cheshire, UK, Indobent Wijaya Mineral of Jakarta, Indonesia, Cia Minera of Lima, Peru, and Southern Clays, Inc. of City of Gordon, Ga.

The free-moisture content of the clay should preferably provide acceptable disinfecting agent stability. Preferably, the free-moisture content should be less than about 4%, about 3%, about 2.5%, or about 1.5% by weight.

Preferred for use herein for providing optimum disinfecting agent stability are pre-dried clays that, in their dessicated form, have the potential to scavenge or pick up moisture. Such clays are described in terms of their so-called 'water-capacity,' defined herein as the equilibrium weight percentage of moisture picked up by a small sample (e.g., about 10 mg) of the dessicated material from air at about 80% relative humidity and about 20° C. as measured by dynamic vapor sorption techniques. For example, if about 10 mg of the dessicated clay picks up about 2 mg moisture, the dessicated clay has a water capacity of about 20%. Preferred for use herein are dessicated clays having a water capacity of at least about 10%, about 15%, or about 18%.

The example compositions illustrated herein preferably include (by weight) from about 1%, about 5%, about 10%, about 15%, about 20%, or about 25%, and preferably to about 80%, about 50%, or about 35% clay.

B. Aluminosilicates

Aluminosilicates can be used herein in place of, or in addition to, clay. The compositions herein can include an aluminosilicate selected from natural and synthetic zeolites, and mixtures thereof. The aluminosilicate is preferably zeolite A, zeolite X, zeolite Y, zeolite P, zeolite beta, faugacite, clinoptililite, silicalite, ZnS5, or like clays supplied by INEOS of Warrington, United Kingdom, UOP of Des Plaines, Ill., and Albermarle of Pasadena, Tex.

Preferably, the free-moisture content of the aluminosilicate is less than about 4%, about 3%, about 2.5%, or about 1.5% by weight.

Preferred for use herein for providing optimum disinfecting agent stability are pre-dried aluminosilicates that, in their dessicated form, have the potential to scavenge or pick up moisture. Such dessicated aluminosilicates can also be described in terms of their so-called 'water-capacity,' as defined hereinabove. Preferred for use herein are dessicated aluminosilicates having a water capacity of at least about 10%, about 15%, or about 18%.

The example compositions illustrated herein preferably include (by weight) from about 1%, about 5%, about 10%, about 15%, about 20%, or about 25%, and preferably to about 80%, about 50%, or about 35% aluminosilicate.

C. Other Inert Water-insoluble Carriers

Inert water-insoluble carriers can be used in place of, or in addition to, clay or aluminosilicates. The compositions illustrated herein can include an inert water-insoluble carrier selected from a group of powdered cellulose, silicas, alumina, activated carbons and mixtures thereof. Nanoparticles of these can also be used.

Preferably, inert water-insoluble carriers include cellulose, preferably an inert water-insoluble carrier is an unmodified cellulose. Preferably, inert water-insoluble carriers include powdered cellulose. Preferably, the free-moisture content of inert water-insoluble carriers should be less than about 4%, about 3%, about 2.5%, or about 1.5% by weight.

The example compositions illustrated herein preferably include (by weight) from about 1%, about 5%, about 10%, about 15%, about 20%, or about 25%, and preferably to about 80%, about 50%, or about 40% inert water-insoluble carriers.

D. Water-soluble Carriers

Water-soluble carriers can be used in place of, or in addition to, clay or aluminosilicates. The compositions illustrated herein can include an inert water-soluble carrier selected from a group of sodium carbonate, potassium carbonate, sodium bicarbonate, potassium bicarbonate, calcium hydroxide, calcium carbonate, and mixtures thereof. Nanoparticles of these can also be used.

The example compositions illustrated herein preferably include (by weight) from about 1%, about 5%, about 10%, about 15%, or about 20%, and preferably to about 80%, about 50%, or about 40% water-insoluble carriers.

In some examples, it may be unnecessary to include a substrate for the disinfecting and/or masking agent.

V. Other Components

The example compositions illustrated herein can include other components as well. For example, one composition includes a nutrient source, such as sources of essential minerals such as iodine, iron or zinc or a source of essential vitamins such as vitamins A, C, etc. A composition fortified with nutrients is valuable to not only provide water that is pure, but that also contains essential minerals and other food additives necessary for health and nutrition.

The food additive or nutrient source can be included as one or more separate compositions or can be incorporated directly into the composition itself. For food additives and nutrient sources that are non-coagulable or that at least partially survive coagulation and flocculation, for example, fluoridating agents, iodinating agents, and essential minerals such as zinc and iron, the food additive or nutrient can be incorporated into the purification composition. Otherwise, the food additive or nutrient sources can also be incorporated in controlled, delayed, sustained or slow release form as described herein with respect to the disinfecting agent.

Other nutrient and/or food additives, such as, for example, B vitamins, including B6, B12, niacin, folic acid, vitamin D, vitamin E, vitamin K, calcium, magnesium, selenium, potassium and molybdenum, can also be added to the composition.

The example compositions disclosed herein can also include a moisture sink to control the free-moisture content of the compositions. This may be advantageous, for example, for disinfecting agents including calcium hypochlorite. Many of the ingredients of the compositions herein, such as the bentonite clays, alum-based coagulants, etc., contain a natural amount of free moisture and this free moisture can be detrimental to calcium hypochlorite stability. In preferred embodiments, therefore, the compositions of the invention preferably has a free-moisture content of less than about 6%, about 4%, or about 2.5% by weight thereof.

It may therefore be desirable to incorporate one or more ingredients that are capable of acting as a moisture sink. For example, low-moisture, pre-dried clays and hydratable salts in anhydrous or partly hydrated form can be used, whereby the free-moisture content of the composition is maintained below the theoretical amount necessary for 100% hydration of the components of the composition. Preferred moisture sinks include pre-dried clays and aluminosilicates, anhydrous sodium carbonate, and mixtures thereof. Preferably the moisture sinks have a free-moisture content of less than about 4%, about 3%, about 2.5%, or about 1.5% by weight.

Free-moisture content of the composition can be determined as follows: (1) a 4 g sample of the composition or moisture sink is extracted into 25 ml of dry isopropanol at room temperature for 10–20 minutes; and (2) a 1 ml aliquot of this solution is then taken and the free moisture determined by a standard Karl Fischer titration. The free moisture is expressed as the percentage weight of water relative to the sample weight (in the example case provided, 4 g).

Free-moisture content of the moisture sink can be determined either as above or preferably by loss on drying at 150° C. In the method a fixed weight of the moisture sink is dried in an oven at 150° C. to constant weight (typically ca. about 2 hours) and the weight loss determined using a standard analytical balance.

VI. Loading The flavorant can be loaded onto the substrate using, for example, a well-known method of spray drying. A preferred method includes the flavor being spray dried using a Tilt-A-Plow spray drying apparatus manufactured by Processall Incorporated of Cincinnati, Ohio, product model number 4H/V. Example equipment parameters used include:

| | |
|---|---|
| Chopper speed = | 2500 rpm |
| Plow speed = | 3000 rpm |
| Run time = | 3–5 minutes |
| Mean power = | 15 kW |
| Injection tube diameter = | 4.75 cm |
| Injection pressure = | 40 psi |

Flavorant loading up to about 10% (w/w) gives a preferred free flowing powder. At about 20% loading, the powder may become sticky. Above this level, a paste may form. Therefore, flavor loading can preferably be less than about 30%, and preferably less than about 20%.

The loaded substrate can be obtained by an example process including the step of (a) contacting a masking component with either a porous or high surface area carrier material, to form a masking agent loaded material. Optionally, the substrate can then be encapsulated by: (b) contacting the loaded substrate with an aqueous solution or dispersion of encapsulating material, to form an intermediate mixture; and (c) drying the intermediate mixture to form an encapsulated substrate. The loaded substrate can be in contact with the aqueous mixture of encapsulating material for a period of time of less than about 120, about 90, about 60, about 30, or about 20 minutes, prior to drying.

The step (a) of contacting masking agent with a suitable substrate (e.g., a porous or high surface area material) to form a loaded substrate can occur in any suitable mixing vessel. Typically, step (a) is carried out in an Schugi, or other high shear mixer, for example a CB mixer available from Gebr. Lödige Maschinenbau GmbH of Paderborn, Germany, although other lower shear mixers, such as a Kenics® KM mixer available from Chemineer, Inc. of Dayton, Ohio, may also be used. Typically, the substrate is passed through the high shear mixer and the masking agent is sprayed onto the porous carrier material.

The adsorption of masking agent onto the porous carrier material is typically an exothermic reaction and heat may be generated during this stage of the process (depending on the masking agent and substrate used). When the substrate is an aluminosilicate, such as zeolite 13x, then a substantial amount of heat can be generated during-step (a). The generation of heat can be controlled by any suitable heat management means; such as placing water jackets or coils on the mixer or other vessel used in step (a), or by direct cooling, for example by using liquid nitrogen, to remove the heat that is generated, and/or by controlling the flow rate of the porous carrier material and masking agent component in the mixer or other vessel used in step (a) to prevent the build up of an excess amount of heat during step (a).

The optional steps (b) and (c) of encapsulation (i.e., of contacting the loaded substrate with an aqueous solution or dispersion of encapsulating material to form an intermediate mixture) can occur in any suitable vessel such as a stirred tank. Alternatively, step (b) can occur in an online mixer. The stirring tank can be a batch tank or a continuous tank. It is preferred to control the temperature of step (b). Preferably, step (b) is carried out a temperature of less than about 50° or less than about 20° C. Cooling means such as a water jacket or liquid nitrogen can be used in step (b) to carry out step (b) at a temperature that is below the ambient temperature.

The step (c) of drying the intermediate mixture to form an encapsulated loaded substrate can be carried out in any suitable drying equipment such a spray-dryer and/or fluid bed dryer. Typically, the intermediate mixture is forced dried (for example, spray-dried or fluid-bed dried) and is not simply left to dry by evaporation at ambient conditions. Typically, heat is applied during this drying step. Typically, the intermediate mixture is spray-dried. Preferably, the temperature of the drying step is carefully controlled to prevent the masking agent component from vaporizing and escaping. Preferably, the intermediate mixture is spray-dried in a spray-drying tower, and the difference between the inlet air temperature and the outlet air temperature in the spray-drying tower is less than about 100° C.

It may be preferred that, during processing and storage thereafter, the loaded substrate and any intermediate product that is formed during processing is kept in an environment having a low relative humidity. Preferably, air immediately surrounding the loaded substrate (or intermediate material thereof) is equal to or lower than the equilibrium relative humidity of the loaded substrate (or intermediate material thereof). This can be achieved, for example, by placing the loaded substrate in air tight containers during storage and/or transport, or by the input of dry and/or conditioned air into the mixing vessels, storage and/or transport containers during the process, transport and/or storage of the loaded substrate (or intermediate material thereof).

Loaded substrates that are obtained by the above process can bind the flavor strongly in product, but release the flavor rapidly on contact with bulk water.

VII. Packaging

The example compositions illustrated herein are preferably in a solid unit dose form, preferably in a tablet or powder form. In a preferred embodiment, the disinfecting agent and the masking agent are delivered at the same time (e.g., the disinfecting and masking agents are combined into a single dose).

Preferably, from about 1 mg, about 200 mg, about 400 mg, about 600 mg, about 800 mg, to about 1000 mg of one example composition disclosed herein (including at least the disinfecting agent and the masking agent) is added to about 1 liter of water. The amount of the composition that is added to the water depends on the impurity of the water. For example, less composition is needed to adequately purify water that is not as impure compared to the amount of composition that is needed to purify very impure water. The amount of the composition that is added to the water also depends on the components included in the composition (i.e., compositions also including a substrate, a primary coagulant, a coagulant aid, a bridging flocculant, a polymeric material, and/or an alkali agent can be larger by weight than a composition including only a disinfecting agent and a masking agent).

In addition, the example compositions are adapted to maintain the potency of the disinfecting agent to thereby reduce recontamination on storage of the purified water. Further, efficiency is increased by combining the purification and masking stages into a single step.

The example composition is preferably packaged so that it is protected from environmental conditions such as moisture. Preferably, the compositions are packaged in a water-impermeable material such as polypropylene or typical laminates. An example of one such laminate is a laminate supplied by Akerlund & Rausing of Sweden, including layers of coated paper (outer), LDPE, aluminium foil and an inner layer Surlyn® (an ethylene/methacrylate co-polymer)—an FDA approved food packaging. For certain applications, child resistant laminates may be preferred.

One example water purification system 100 is shown in FIG. 1. The system 100 includes a container 110 holding a volume of water for treatment and a package 120 enclosing an example composition including a disinfecting agent and a masking agent (in the illustrated embodiment, formed into tablets).

One example of such a system that can be used in conjunction with the example compositions disclosed herein is described in PCT Application Ser. No. WO 02/40414, entitled "Water Purifying Kits" and filed on Sep. 28, 2001, assigned to the same assignee as the present invention.

The example compositions illustrated herein are particularly suited to disinfecting water on a scale appropriate for one or several individuals (i.e., larger in scale than a single drinking serving, but smaller in scale than a water treatment plant). For example, the package 120 can preferably hold composition sufficient to treat water of volumes ranging from about 0.5 liter, about 1 liter, about 10 liters, about 1000 liters, or about 10,000 liters. For example, the package 120 can include composition sufficient to treat 10 liters of water, which is approximately sufficient for treating water for a family of about five people for about 1 to about 2 days (assuming an average consumption of approximately about 1 to about 2 liters of water per day per person).

VIII. Shelf Stability

The example compositions illustrated herein are preferably stable for a given period before use, or, in other words, have a known shelf life. For example, for one example composition including a chlorine-based disinfecting agent and a masking agent, loaded at a level of about 5% onto a substrate that in turn makes up a small percentage of the finished product weight, chlorine loss is about 17% after about 2 weeks at about 60° C. It is preferable to obtain less than about 20% loss on storage safter about 2 years at about 30° C.

Shelf life preferably lasts for at least two years. For the example compositions shown, the preferred loss of active chlorine (i.e., activity loss) is less than about 20% or about 25% on shelf over about two (2) years, assuming an ambient temperature of about 25° C. or about 30° C., or less than about 20% or about 25% after about one (1) month at about 50° C.

IX. Diluted Stability

The diluted stability is preferably such that there is less than a about 20% or about 10% difference in degradation (judged versus a control sample containing no flavorant) of the disinfecting agent in treated water over a relevant time period, such as about one hour, about one day, or about two days. In the example compositions illustrated herein, degradation was approximately about 6%.

This approach contrasts sharply to adding fruit juice to water to enhance taste. Illustrated below in Table 1 is the effect of adding freshly squeezed fruit juices to water containing approximately about 2 ppm of residual free chlorine. In each case, approximately about 0.5 ml aliquots were added to separate 1 liter portions of an about 2 mg/l free chlorine solution in tap water. The level of addition was chosen to give similar odor masking to that offered by the preferred masking agents disclosed herein. Free chlorine measurements were taken about two (2) minutes after addition, and again after about 24 and about 48 hours. These measurements show a marked decline in chlorine concentration relative to the standard.

TABLE 1

| Sample | Free chlorine/ppm | | | |
|---|---|---|---|---|
| | Before addition | 2 minutes after addition | 24 hours after addition | 48 hours after addition |
| Control | 2 | 1.9 | 0.9 | 0.5 |
| Orange | 1.9 | 1 | 0.2 | <0.1 |
| Lime | 2 | 0.9 | 0.1 | <0.1 |
| Grapefruit | 1.9 | 0.9 | <0.1 | <0.1 |
| Lemon | 2 | 1.1 | <0.1 | 0.1 |

Chlorine concentrations were assayed using standard methods, combining reaction with DPD & concentration assay via a suitable meter. One such suitable meter is the Hanna free chlorine meter.

By contrast, the approaches disclosed herein are predicated on masking of chlorine. When the masking agent is loaded into a preferred substrate and mixed with a typical water purification composition (combined flocculant/disinfectant), results such as those outlined below in Table 2 are obtained.

TABLE 2

| Sample | [Cl2] after treatment (30 mins)/ppm | [Cl2] after addition (24 hours)/ppm | [Cl2] after addition (48 hours)/ppm |
|---|---|---|---|
| Control | 1.7 | 1.2 | 0.9 |
| Masking agent | 1.7 | 1.2 | 0.9 |

As can be seen from the above table, there is little difference in chlorine profile between the control sample (i.e. no masking agent) and the sample containing the masking agent. Consequently the treated water maintains its protection from recontamination for extended periods of time.

In one preferred embodiment, the composition provided a meaningful 1-day residual chlorine content of at least about 0.2 ppm.

X. Method of Use

The compositions disclosed herein can be used to purify water using a method including the step of contacting the composition herein to water to obtain partially purified water which is substantially free from the taste or odor of the disinfecting agent.

More particularly, one example method includes contacting the composition herein including the disinfecting agent to water to obtain partially purified water including solid matter; introducing a masking agent to mask any undesired taste or odor associated with the composition; and removing at least part of said solid matter from said partially purified water by: (i) filtration; (ii) decanting; (iii) sedimentation; (iv) flotation; or (v) a combination thereof, to obtain purified water.

Figure 2:
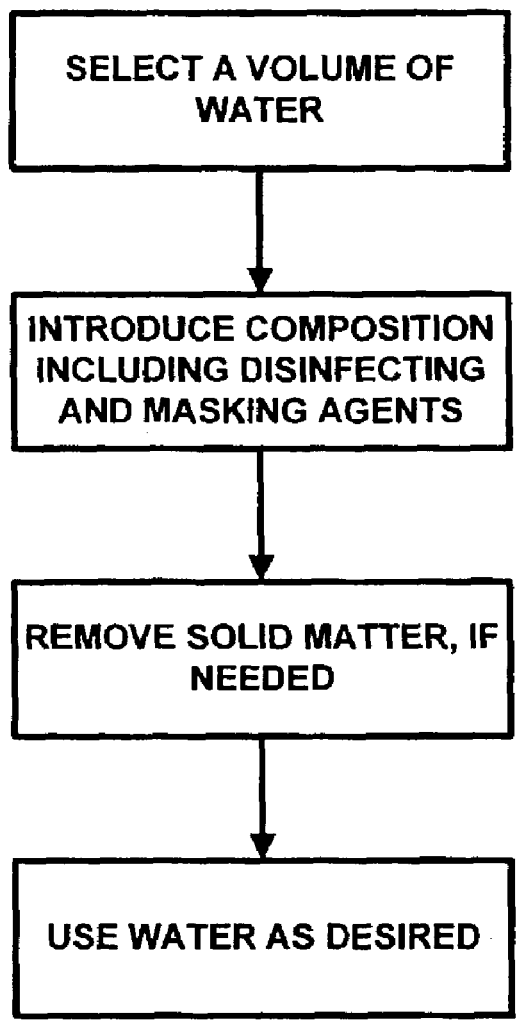
FIG. 2 is a flow diagram illustrating one example method of treating water in accordance with an embodiment of the present invention.

The disinfecting and masking steps can preferably be performed in a single step using a composition including both the disinfecting agent and the masking agent, as illustrated in FIG. 2. Alternatively, the steps can be performed separately. For example, the water can be disinfected by introducing the disinfecting agent into the water, and then taste and odor associated with the disinfecting agent can be minimized by introducing the masking agent.

XI. EXAMPLES

The following example compositions A–X illustrated in Tables 3–5, utilizing citrus extracts such as lime, lemon, tangerine, or orange as masking agents, are in accord with the present invention. All percentages are by weight of composition.

TABLE 3

| | A | B | C | D | E | F | G | H |
|---|---|---|---|---|---|---|---|---|
| Chitosan | | | 2 | | 1 | 1 | 2 | 1 |
| Cationic modified potato starch | 1 | | | | | | | |
| Magnafloc LT20 | | | 1 | | | 1 | 0.8 | |

TABLE 3-continued

|  | A | B | C | D | E | F | G | H |
|---|---|---|---|---|---|---|---|---|
| Magnafloc LT25 |  | 1 |  | 2 |  |  |  | 0.4 |
| Magnafloc LT28 | 5 |  |  |  |  |  | 0.7 |  |
| Aluminium sulphate | 20 |  |  |  | 30 |  |  | 35 |
| Iron III sulphate |  | 38 | 35 | 38 |  | 33 | 36 |  |
| Calcium hypochlorite |  | 1 | 0.8 | 0.85 | 1.5 | 0.9 | 1.3 | 1.2 |
| Iodate |  |  |  | 0.02 |  |  | 0.01 |  |
| Zinc Sulphate |  |  |  |  | 3.5 |  |  |  |
| Hectorite clay |  |  | 25 |  | 49 |  | 36 | 27 |
| Montmorillonite clay | 63.8 | 35 |  | 35 |  | 48 |  |  |
| Masking Agent | 0.01 | 0.02 | 0.03 | 0.05 | 0.02 | 0.04 | 0.07 | 0.005 |
| Sodium carbonate | 10 | 24 |  | 24 | 13 | 15 | 23 |  |
| Sodium bicarbonate |  |  | 35 |  |  |  |  | 35 |
| Potassium Permanganate |  | 0.02 |  |  | 0.03 |  | 0.04 |  |
| Miscellaneous | to 100 | to 100 | to 100 | to 100 | to 100 | to 100 | to 100 | to 100 |

TABLE 4

|  | I | J | K | L | M | N | O | P |
|---|---|---|---|---|---|---|---|---|
| Chitosan |  | 0.5 |  | 0.5 |  | 1 |  | 1 |
| Cationic modified potato starch | 2 |  |  |  | 2 |  |  |  |
| Magnafloc LT20 |  | 0.8 |  |  | 1 | 0.3 |  |  |
| Magnafloc LT25 |  |  | 0.7 | 0.9 |  |  |  |  |
| Magnafloc LT28 | 1.2 |  |  |  |  |  | 0.5 | 0.9 |
| Aluminium sulphate | 35 |  |  |  |  |  |  | 40 |
| Iron III sulphate |  | 35 | 45 | 40 | 46 | 32 | 35 |  |
| Calcium hypochlorite | 1.5 | 0.9 | 0.8 | 1.5 | 0.5 | 0.9 | 1 | 1.5 |
| Iodate | 0.02 | 0.02 |  |  |  | 0.04 |  |  |
| Zinc Sulphate | 4 |  |  |  |  |  |  |  |
| Hectorite clay |  |  |  |  |  | 44 | 35 |  |
| Montmorillonite clay |  | 40 | 23 | 32 | 22 |  |  |  |
| Zeolite X | 34 |  | 2 |  |  |  | 3 | 20 |
| Masking Agent | 0.02 | 0.03 | 0.05 | 0.03 | 0.03 | 0.04 | 0.03 | 0.01 |
| Sodium carbonate | 22 | 22 | 28 | 25 | 28 | 21 | 25 |  |
| Sodium bicarbonate |  |  |  |  |  |  |  | 36 |
| Potassium Permanganate | 0.02 | 0.015 | 0.01 |  | 0.01 |  | 0.05 | 0.01 |
| Miscellaneous | to 100 | to 100 | to 100 | to 100 | to 100 | to 100 | to 100 | to 100 |

TABLE 5

|  | Q | R | S | T | U | V | W | X |
|---|---|---|---|---|---|---|---|---|
| Chitosan |  |  | 2 |  |  |  |  |  |
| Cationic modified potato starch |  | 0.7 |  |  |  |  |  |  |
| Magnafloc LT20 |  | 1 |  |  |  |  | 3 |  |
| Magnafloc LT25 | 0.7 |  | 1 | 0.3 |  |  |  |  |
| Magnafloc LT28 |  |  |  |  |  |  |  |  |
| Aluminium sulphate |  | 36 |  |  |  |  |  |  |
| Iron III sulphate | 39 |  | 37 | 42 |  |  |  |  |
| Calcium hypochlorite | 0.85 | 1 | 1 | 0.9 | 50 | 20 | 30 | 20 |
| Iodate |  |  |  |  |  |  |  |  |
| Zinc Sulphate |  |  |  |  |  |  | 5 |  |
| Hectorite clay |  |  |  |  | 20 |  |  |  |
| Montmorillonite clay | 35 |  | 34 | 30 |  | 20 | 20 | 50 |
| Zeolite X |  | 39 |  |  | 20 |  |  |  |
| Masking Agent | 0.01 | 0.03 | 0.02 | 0.01 | 1 | 1 | 1 | 1 |
| Sodium carbonate | 24 | 22 | 24 | 26 |  |  |  |  |
| Sodium bicarbonate |  |  |  |  | 8 | 53 | 25 | 18 |
| Potassium Permanganate | 0.015 |  | 0.03 | 0.04 |  |  |  |  |
| Potassium Carbonate |  |  |  |  |  |  | 10 | 9 |
| Miscellaneous | to 100 | to 100 | to 100 | to 100 | to 100 | to 100 | to 100 | to 100 |

In the above examples, calcium hypochlorite is added in granular form preferably including particles of about 650 μm median particle size with less than about 10% by weight larger than about 1400 μm, less than about 0.5% by weight larger than about 2000 μm, and less than about 15% by weight smaller than about 150 μm. The free-moisture content of the compositions was in the range from about 0% to about 4%. The hectorite clay, montmorillonite clay and zeolite X were all pre-dried to a free-moisture content below about 1.5% by weight and had a water capacity in excess of about 18%. The compositions have a $t_{max}$ (i.e., the time for achieving maximum disinfectant concentration after addition to deionized water at about 20° C.) of at least about 3 minutes and a $t_{80}$ (i.e., about the 80th percentile soluble organic flocculation rate) of less than about 60 seconds. In the examples, about 4 g of compositions A to T or about 0.05 g to about 0.25 g of products U to X were added in powder form, usually from unit dose trilaminate packages to about 10 liters of water.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the instant specification.

What is claimed is:

1. A method for masking undesired taste and odor characteristics of a disinfecting agent in a volume of water while preserving disinfecting activity of the disinfecting agent, the method comprising:
   (a) adding an effective amount of a chlorine-based disinfecting agent to water;
   (b) adding an effective amount of a chlorine-compatible masking agent loaded onto a substrate to the water; and
   (c) allowing an effective amount of the masking agent to be released from the substrate to mask the undesired taste and odor of the disinfecting agent in the water.

2. The method of claim 1, wherein the masking agent includes a citrus fruit derived flavor.

3. The method of claim 1, wherein the substrate is selected from the group consisting of clays, zeolites, water-soluble carriers, water-insoluble carriers, and mixtures thereof.

4. The method of claim 1, wherein the substrate has an aperture size from about 4 to about 100 angstroms.

5. The method of claim 1, wherein the substrate is loaded with about 0.5% to about 20% weight of the masking agent.

6. The method of claim 1, wherein a total amount of the masking agent released into the water is about 10 ppb to about 2000 ppb.

7. The method of claim 1, wherein activity loss of the disinfecting agent is less than about 25% after a shelf life of about two (2) weeks at 60 degrees Celsius.

8. The method of claim 1, wherein activity loss of the disinfecting agent is about 20% weight less than a control sample without the masking agent.

9. The method of claim 1, wherein at least about about 20% weight of the masking agent is released into the water within about two (2) minutes.

10. A composition for disinfecting drinking water, the composition comprising:
    (a) a halogen-based disinfecting agent;
    (b) a halogen-compatible masking agent operable to mask the halogen-based disinfecting agent in drinking water;
    (c) a substrate, wherein the masking agent is loaded on the substrate.

11. The composition of claim 10, wherein the halogen-based disinfecting agent includes chlorine or a chlorine-based derivative.

12. The composition of claim 11, wherein the halogen-based disinfecting agent includes calcium hypochlorite.

13. The composition of claim 10, wherein the masking agent includes citrus fruit derived flavor.

14. The composition of claim 13, wherein the masking agent is selected from the group consisting of lime, lemon, orage, tangerine, grapefruit, begamont, and mixture thereof.

15. The composition of claim 10, wherein the masking agent includes a terpene-free citrus fruit derived flavor.

16. The composition of claim 1, wherein the substrate is selected from the group consisting of clays, zeolites, other water-insoluble carriers, water-soluble carriers, and mixtures thereof.

17. The composition of claim 1, wherein the substrate is an inorganic, hydrophilic swelling material.

18. The composition of claim 17, wherein the substrate is selected from the group consisting of laponite, hectorite, montmorillonite, nontronite, saponite, volkonsite, sauconite, beidellite, allevarlite, illite, halloysite, attapulgite, and mixtures thereof.

19. The composition of claim 1, wherein the substrate has an aperture size from about 4 to about 100 angstroms.

20. The composition of claim 1, wherein the substrate is loaded with about 0.5% by weight to about 20% by weight of the masking agent.

21. The composition of claim 1, wherein the substrate is activated by drying to less than 5 percent moisture by weight, as measured by loss on drying at 150° Celsius.

22. The composition of claim 1, wherein activity loss of the disinfecting agent is less than about 50% by weight for a shelf life of the composition.

23. The composition of claim 1, wherein the composition is contained in a package, the package preserving the composition from the outer environment.

24. The composition of claim 1, further comprising a moisture sink, wherein the composition has a free-moisture content of less than about 4% by weight.

25. A composition for purifying water, the composition comprising:
    (a) a primary coagulant;
    (b) a chlorine-based disinfecting agent; and
    (c) a chlorine-compatible masking agent loaded onto a substrate and operable to mask the chlorine-based disinfecting agent in potable water.

26. The composition of claim 25, wherein the primary coagulant is selected from the group consisting of water-soluble, multivalent inorganic salts and mixtures thereof.

27. The composition of claim 25, further comprising a bridging flocculant selected from the group consisting of water-soluble and water-dispersible anionic and nonionic polymers having a weight average molecular weight of at least about 2,000,000, and mixtures thereof.

28. The composition of claim 27, further comprising a water-soluble alkali.

29. The composition of claim 25, further comprising a food additive.

30. The composition of claim 25, further comprising a coagulant aid selected from the group consisting of water-soluble and water-dispersible cationic polymers, and mixtures thereof, having an average molecular weight of less than about 1,500,000.

31. The composition of claim 25, further comprising a water-insoluble silicate selected from the group consisting of clays, zeolites, and mixtures thereof.

32. The composition of claim 25, wherein the disinfecting agent comprises calcium hypochlorite.

33. The composition of claim 25, further comprising a moisture sink, wherein the composition has a free-moisture content of less than about 4% by weight.

34. A water treatment composition comprising:
    (a) a chlorine-based disinfecting agent operable to disinfect water such that the water is potable; and
    (b) a chlorine-compatible masking agent in an amount sufficient to provide a meaningful 1-day residual chlorine content and a chlorine odor detection threshold of at least 0.5 ppm in the potable water.

35. The composition of claim 34, wherein the masking agent is loaded onto a substrate.

36. The composition of claim 34, further comprising a moisture sink, wherein the composition has a free-moisture content of less than about 4% by weight.

* * * * *

UNITED STATES PATENT AND TRADEMARK OFFICE
CERTIFICATE OF CORRECTION

PATENT NO. : 7,153,438 B2 Page 1 of 1
APPLICATION NO. : 10/371864
DATED : December 26, 2006
INVENTOR(S) : Philip Frank Souter et al.

It is certified that error appears in the above-identified patent and that said Letters Patent is hereby corrected as shown below:

Column 11
Line 11, please delete "to".
Line 25, please delete "200" and insert -- 20° --.

Column 19
Line 16, please delete "safter" and insert -- after --.

Col. 23 lines 57-59 Claim 14
Please delete "orange, tangerine, grapefruit, begamont, and mixture thereof" and insert -- orange, tangerine, grapefruit, bergamot, and mixtures thereof --.

Signed and Sealed this

Tenth Day of June, 2008

JON W. DUDAS
*Director of the United States Patent and Trademark Office*